United States Patent [19]

Long

[11] Patent Number: 4,955,242

[45] Date of Patent: * Sep. 11, 1990

[54] CONVEYOR BELT CROSS-STREAM SAMPLING SYSTEM AND ASSOCIATED METHOD

[76] Inventor: John B. Long, 421 Heron Hill Dr., Louisville, Tenn. 37777

[*] Notice: The portion of the term of this patent subsequent to Apr. 24, 2007 has been disclaimed.

[21] Appl. No.: 452,113

[22] Filed: Dec. 15, 1989

Related U.S. Application Data

[63] Continuation of Ser. No. 363,544, Jun. 6, 1989, Pat. No. 4,919,000.

[51] Int. Cl.⁵ ............................................. G01N 1/12
[52] U.S. Cl. ................................................. 73/863.91
[58] Field of Search ........... 73/863.91, 863.92, 864.32, 73/864.31

[56] References Cited

U.S. PATENT DOCUMENTS 4,790,196  12/1988  Gould ................................. 73/863.91

FOREIGN PATENT DOCUMENTS

742752  6/1980  U.S.S.R. ............................ 73/863.91
828007  5/1981  U.S.S.R. ............................ 73/863.91

Primary Examiner—Robert Raevis
Attorney, Agent, or Firm—Luedeka, Hodges & Neely

[57] ABSTRACT

A method and apparatus are disclosed for cross-stream samnpling of bulk material from a conveyor belt. The apparatus includes a sampler movable across the conveyor belt for segregating a cross-stream increment of bulk material from the belt and ejecting the sample into a collection chute positioned adjacent the belt. The sampler has a trapezoidal cross-section so that the surface area which is projects upstream of the bulk material flow is relatively small in comparison to its sample-accepting capacity. The system also includes a surge dam positioned upstream of the sampler for limiting buildup of bulk material against the upstream side of the sampler. Upon completion of an increment-collecting cycle, the sampler is parked in a position relative to the opening of the collection chute so that ingress of bulk material into the chute opening from the belt is restricted by the sampler.

8 Claims, 4 Drawing Sheets

CONVEYOR BELT CROSS-STREAM SAMPLING SYSTEM AND ASSOCIATED METHOD

This is a continuation of application Ser. No. 07/363,544, filed June 6, 1989, now U.S. Pat. No. 4,919,000.

This invention relates generally to the mechanized sampling of bulk material and relates, more particularly, to cross-stream sampling of bulk particulate material from a conveyor belt.

The type of sampling system with which this invention is concerned includes a sampler mounted for rotation about an axis above a conveyor belt and means for rotating the sample so that as the sampler moves through a complete revolution, it traverses the belt in a manner segregating and removing a cross-stream increment of bulk material from the belt. The sampler includes spaced apart upstream and downstream side plates having leading edges which move into the bulk material in advance of the remainder of the plates and a back plate or sweep joined between the side plates rearwardly of the leading edges. As the sampler is moved through the bulk material, the side plates segregate a cross-stream increment of the material, and the back plate sweeps the segregated increment from the belt. Commonly, the side plates are relatively broad as viewed along the path of material movement so that an increment which is representative of substantially the entire cross-section of the material is segregated and removed for sampling. For collection of the increment removed from the belt, collection means, such as a chute, is positioned with its sample-receiving opening adjacent the belt.

Exemplary systems of the aforedescribed type are shown and described in issued U.S. Pat. Nos. 4,619,149 and 4,796,476. The systems of these patents are particularly well-suited for obtaining cross-stream samples from a moving belt, and are thus especially useful in sampling from lengthy high-capacity belts where intermittent stopping and starting for sampling purposes would be impracticable.

A limitation associated with sampling systems of the aforedescribed type when used to remove a sample from a moving belt relates to the continual movement of bulk material against the upstream side of the sampler as the sampler passes through the bulk material. Such continued movement of material generates a columnar thrust force upon the sampler which could be damaging to the sampler or its structural supports and may generate drag forces upon the belt which could expose the belt to excessive pull. Moreover, problems attendant this continual movement of bulk material against the sampler are compounded if the sampler stalls while moving across the belt so that the sampler remains positioned in the path of material flow. With the sampler stalled in the path of material flow, material builds up against the upstream side of the sampler and thus increases the thrust forces upon the sampler and the drag forces upon the belt. In an application in which a high-capacity belt is delivering, for example, one hundred tons per minute and moving at a speed of about one thousand feet per minute, it will be appreciated that the buildup of material against a stalled sampler will rapidly generate tremendous thrust and drag forces.

Another limitation of the aforedescribed systems relates to the normally open collection means, or chute, positioned adjacent the belt for collecting the increment removed by the sampler. While the chute must be opened for receiving material when swept from the belt by the sampler, the open chute is susceptible to receiving particulate material which may accidentally fall from the belt during the period of time between increment-collecting cycles. Of course, material which falls into the chute between increment-collecting cycles may bias, or contaminate, subsequently-obtained samples.

It is an object of the present invention to provide a new and improved sampling system for obtaining a cross-stream increment of bulk material from a moving conveyor belt which reduces any likelihood of damage to the system or the belt from material which may build up against the sampler during the course of an increment-collection operation.

Another object of the present invention is to provide such a system for limiting the amount of bulk material which may build up against the sampler as it passes across the belt or stalls in the path of material flow.

Still another object of the present invention is to provide such a system which reduces any likelihood of material spillage which may otherwise occur as a result of buildup of material against the sampler during an increment-collecting operation.

Yet another object of the present invention is to provide such a system and method for preventing incidental bias of a sample due to the ingress of material from the belt into a collection chute or the like between increment-collection cycles.

These and other objects and advantages of the invention will become apparent upon consideration of the following detailed description when considered in conjunction with the accompany drawings in which.

This invention resides in a system for taking a cross-stream increment of bulk material moving along a conveyor belt. The system comprises a sampler, means for supporting the sampler for rotation about an axis, and means for rotating the sampler about its axis so that the sampler moves across the conveyor belt at substantially a right angle with respect to the direction of movement of bulk material flow and passes through the bulk material in a manner segregating and removing a cross-stream increment of bulk material from the belt. During a pass of the sampler through the material, the sampler enters the bulk material at one side of the belt corresponding to the sweep-entry-side of the belt and exits the bulk material at the other side of the belt corresponding to the sweep-eject side of the belt. Collection means for collecting the cross-stream increment removed from the belt by the sampler has an opening adjacent the sweep-eject side of the belt for receiving the cross-stream increment of bulk material removed from the belt by the sampler. The sampler projects a relatively small area upstream of the bulk material flow so that the sampler surface area against which the bulk material is permitted to flow is relatively small. The system also includes limiting means for limiting the buildup of bulk material against the upstream side surface of the sampler. Furthermore, the system includes control means for halting the rotation of the sampler and disposing the sampler adjacent the sweep-eject side of the belt upon completion of an increment-collecting cycle so that ingress of bulk material into the collection means opening from the belt between increment-collecting cycles is restricted by the sampler.

Figure 1:
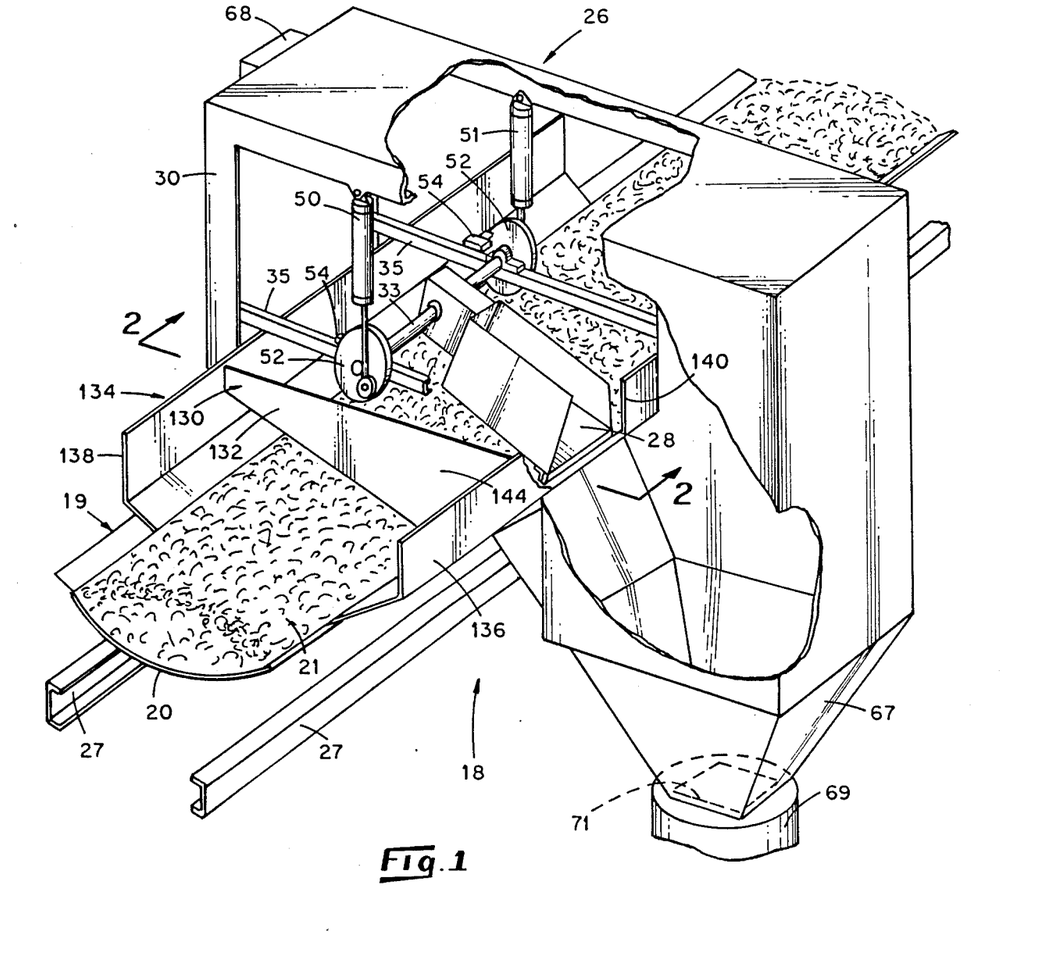
FIG. 1 is a perspective view, with certain parts broken away to show construction details, of a belt conveyor with which an embodiment of a sampling system in accordance with the invention is utilized.

Referring now to the drawings in which like reference numerals refer to like or similar parts throughout the several views, FIG. 1 illustrates a typical environment in which an embodiment of a sampling system, generally indicated 18, is used. Such an environment includes a belt conveyor 19 including a continuous belt 20 supported upon a plurality of idlers 24 (FIG. 2) for transporting a stream of bulk particulate material 21 along the belt length. The system 18 includes a sampling apparatus 26 including a sampler 28 mounted for rotation about an axis above the belt 20 by means of a frame structure 30 straddling a conveying reach 22 (FIG. 2) of the belt 20. The sampler 28 is thus supported in position for removing a cross-stream increment from the belt reach 22 as the sampler is rotated about its axis. Suitable collection means, such as chute 69, is positioned to one side of the belt 20 for receiving the bulk material increment removed from the belt 20 by the sampler 28.

As will be described in greater detail hereinafter, the sampler 28 is shaped so that the area which it projects upstream of the bulk material flow is relatively small in relation to its sample-accepting capacity. Therefore, the surface area against which the flow of bulk material is permitted to act as the sampler 28 moves across the belt 20 is relatively small. In addition, the system 18 includes a surge dam 130 positioned upstream of the sampler 28 for limiting the buildup of bulk material against the sampler 28 as it moves across the belt 20. Moreover and as is described in greater detail herein, an increment-collecting cycle is concluded by parking the sampler 28 adjacent the chute-side of the belt 20 so that the opening of the chute 69 is covered by the sampler 28 in a manner preventing ingress of bulk material from the belt 20. The sampler is thereafter maintained in its parked positioned until a subsequent increment-collection cycle is initiated.

The belt 20 is appropriately supported by the idlers 24 in a transverse trough-like configuration (FIG. 2) in a conventional manner so that the reach 22, viewed in cross-section, has opposite sides which are angled relative to a center section. The belt 20 is driven by any suitable means as, for example, a drive motor, located adjacent an end of the belt 20. The idlers 24 are, in turn, rotatably supported by a suitable fixed-frame structure 27 (FIG. 1).

Figure 2:
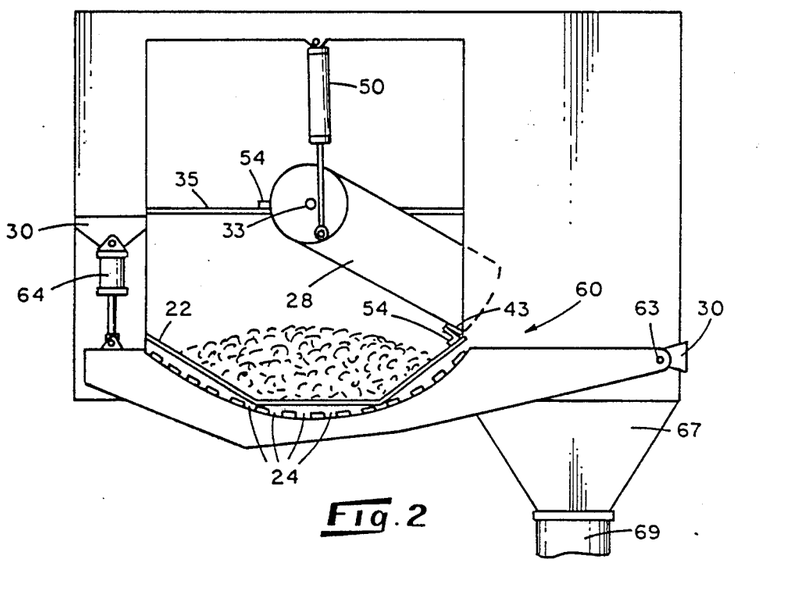
FIG. 2 is a diagrammatic view of the FIG. 1 system as seen along line 2—2 of FIG. 1 illustrating the position of the sampler of the system at the completion of an increment-collection cycle.

With reference still to FIGS. 1 and 2, the sampler 28 is rotatable relative to the frame structure 30 in a plane substantially perpendicular to the direction of movement of the conveying reach 22 and thus moves transversely of the belt 20. Frame structure 30 includes a base which, in the depicted system 18, is secured to the fixed-frame structure 27 of the belt conveyor beneath the conveying reach 22. Sampler 28 is preferably fixedly attached to a shaft 33 which is rotatably mounted on transversely-extending support members 35 extending across opposite sides of the frame structure 30 and spaced apart longitudinally of the direction of movement of the belt 20. Thus, the shaft 33 is supported over and above the conveying reach 22 and aligned parallel to the line of movement of the belt 20.

In order to effect rotation of the shaft 33 and the sampler 28, the opposite ends of the shaft 33 are appropriately connected to double-acting pneumatic cylinders 50 and 51 through discs 52 provided on the shaft ends. By introducing air into the cylinders 50 and 51 in a sequential manner to thereby move the piston rods of the respective cylinders 50 and 51 between extended and retracted conditions, the cylinders 50 and 51 force the shaft 33 and thus the sampler 28 to rotate at a very high speed across the belt to remove a representative sample from a fast moving belt and so that the sampler 28 is moved under power from the cylinders 50 and 51 throughout its pass across the belt 20. In contrast to sample removal systems in which sampler braking is dependent upon load resistance encountered as a part of the process by which the sampler is slowed to a stop, it has been found that the speed with which the sampler 28 crosses a load stream is only minimally affected by varying amounts of resistance encountered with varying rates of flow.

Braking of the sampler 28 is accomplished by appropriate control of the flow of air into the cylinders 50 and 51 so that, as it explained in greater detail herein, the sampler 28 parks in a preselected position between increment-collecting cycles. Braking means 54 are mounted and are appropriately connected to the cylinders 50, 51 for operation in case of a loss of air pressure upon the support members 35. The braking means 54 are spring-operated and air released and includes pneumatically-actuated calibers for acting against the surfaces of the discs 52 to hold the sampler 28 in a raised position relative to the conveying reach 22 so that the sampler 28 cannot slip down and interfere with the material flow. It will be understood, however, that as long as the system air pressure is maintained, the braking means 54 do not operate. For a more detailed description of the interconnection between the pneumatic cylinders 50 and 51, braking means 54 and the sampler 28, reference can be had to U.S. Pat. No. 4,796,476 whose disclosure is incorporated herein by reference.

Figure 3:
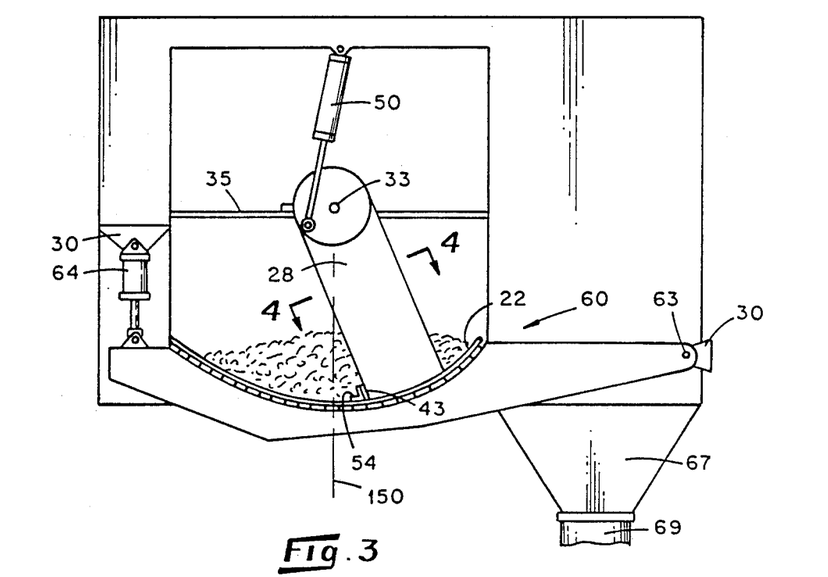
FIG. 3 is a view similar to that of FIG. 2 illustrating a position of the sampler during an increment-collection cycle.

With reference still to FIGS. 2 and 3, the sampling system 18 further includes a contour plate assembly 60 for lifting and contouring the conveying reach 22 so that the reach 22 has a transverse arcuate configuration which substantially conforms to the radius of the arc as circumscribed by the sampler 28 as it moves across the reach 22. The plate assembly 60 includes a pair of spaced-apart contour beams pivotally mounted as at 63 on the frame structure 30 and connected at its other end to the rods of pneumatic cylinders 64 (only one shown in FIGS. 2 and 3). The pneumatic cylinders 64 are in turn attached to the frame structure 30 by pivot pins so that actuation of the cylinders 64 raises one end of the beam about the pivotal connection at 63 from a position, illustrated in FIG. 2, to a raised position, illustrated in FIG. 3, at which its arcuate configuration substantially conforms the reach 22 to the radius of the arc circumscribed by the radially-outermost edge of sampler 28 as it moves across the reach 22. Thus, the assembly 60 modulates the normal troughing of the conveying reach 22 in a manner facilitating a clean sweep of the sampler 28 across the belt 20. For a more complete description of the plate assembly 60, reference may be had to the referenced U.S. Pat. No. 4,619,149, the disclosure of which is incorporated herein by reference.

With reference again to FIG. 1, one side of the frame structure 30 supports a housing 67 for directing the material comprising the increment removed from the belt 20 into the chute 69 through which it is discharged for further treatment. In the depicted system 18, the chute 69 defines an upwardly-directed opening 71 which remains in an open condition for receipt of the material increment removed from the belt 20.

Control means 68 are mounted on the frame structure 30 of the sampling apparatus 26 for systematic operation of the system 18. More particularly, the control means 68 sequentially actuates the contour plate assembly 60 to raise and conform of the conveying reach 22 of the belt 20 to an arcuate configuration, selectively actuates the cylinders 50 and 51 to impart a rotational force on the sampler 28 causing the latter to rotate on the shaft 33 to segregate and remove a cross-stream increment of bulk material from the contoured reach 22 and then return the sampler 28 to the park position, actuates braking means 54 to hold the sampler 28 in the park position after removal of the cross-stream increment, and lowers the contour plate assembly 60 to resume normal troughing of the conveying reach 22 by the idlers 24. Preferably, the control means 68 includes a control computer which is preset in accordance with predetermined timing or location as to sample taking, free of selection on a discretionary basis by an operator, and is operative so that the systematic and sequential operation thereof is performed within a relative short period of time.

With reference to FIGS. 1-4, the sampler 28 includes upstream and downstream side or divider plates 34 and 36, respectively, which are each rigidly attached to the shaft 33 for rotation therewith. In the context of this invention, the term "upstream" refers to the location from which the particulate material moves on the belt 20, and the term "downstream" refers to the location to which the particulate material is being taken by the belt 20. During an increment-collecting cycle, the side plates 34 and 36 are rotated together about the shaft 33 in a counterclockwise direction as viewed in FIGS. 2 and 3 and, in this connection, include leading edges 40, 42 which enter the bulk material in advance of the remainder of the plates 34 and 36 during each pass of the sampler 28 through the material. The leading edges 40, 42 are generally aligned with one another as the sampler 28 is viewed from a distal location upstream of the system 20 and spaced a preselected distance apart for a reason apparent herein. In the depicted system 20, the leading edges 40, 42 are parallel to one another so as to lie in a plane oriented generally parallel to the rotational axis of the shaft 33 and thus the direction of movement of the bulk material carried by the belt 20. The radially outwardmost point on each leading edge 40 or 42 defines the extremity of the path of arcuate movement of the sampler 28 about the shaft 33.

The sampler 28 also includes a back plate or sweep 41 positioned between the plates 34, 36 for sweeping material from the belt 20 as the sampler 28 passes thereacross. Thus, the side plates 34, 36 and back plate 41 together define a sample-accepting cavity for collecting a cross-stream increment of the material separated by the leading edges 40, 42 as the sampler 28 is swept thereacross. Upon completion of a pass of the sampler 28 through the bulk material and, as illustrated in FIG. 2, the back plate 41 is in a position for ejecting the collected increment off of the outermost edge of the back plate 41 and into the chute 69. In the depicted system 18, an increment is ejected as a body by forward inertia, rather than by centrifugal force. The slinging of material which normally accompanies centrifugal force-ejection may result in the slinging of material back into the flow, thus biasing the sample. By comparison, the ejection of material by forward inertia does not "sling" the material, and the system 18 provides an advantage in this report.

Preferably, wiper means 43 (FIGS. 2 and 3) fabricated from a deformable material arc mounted to the rearward side of the back plate 41 so as to trail the sampler 28 and substantially remove any bulk material remaining on the reach 22 as the sampler 28 is rotated through the material. In addition, a sealing angle member 54 having a trailing flange of about three inches in length is bolted across the back of the plate 41 for sealing the space between the upper surface of the belt 20 and the remainder of the sampler 28. As will be apparent herein, the sealing member 54 prevents the passage of bulk material between the sampler 28 and the belt 20 when the sampler 28 is parked adjacent the chute opening 71.

In one aspect of the present invention and as mentioned earlier, the sampler 28 is shaped so that the area which it projects upstream of the bulk material flow, or the frontally-projected area of the sampler 28 as viewed in FIGS. 2 or 3, is relatively small in relation to its sample-accepting capacity so that the sampler 28 provides a relatively small surface area against which the bulk material is permitted to flow as the sampler moves across the belt 20. To this end and as viewed in FIG. 4, the side plates 34, 36 are disposed at an angle in relation to one another and so that one of the plates 34 or 36 forms an acute angle with the back plate 41. In the illustrated sampler 28, the upstream plate 34 is arranged at a right angle to the back plate 41, and the downstream plate 36 forms an acute interior angle 44 with the back plate 41. Thus, the sample-accepting cavity, bounded by the walls of the side plates 34, 36 and back plate 41 and a plane containing the leading edges 40 and 42 has a trapezoidal cross section as viewed in FIG. 4.

Preferably, the acute angle 44 is determined as a function of the anticipated rate of the sampler 28 across the belt 20 and the anticipated speed of the belt 20 while the sample is being taken so that the downstream plate 36 encounters no appreciable resistance to movement across the belt 20 by the bulk material and at the same time contributes to the maximizing of the volumetric capacity of the sampler 28. Thus, the acute angle 44 is calculated so that the plane of the downstream plate 36 is arranged generally parallel to the downstream edge of the path left in the material following traversal of the sampler 28 through the bulk material.

For a sample-taking application during which the sampler 28 is expected to move across the belt 20 at about 240 inches per second and the belt 20 has a width of 48 inches and moves at about 600 feet per minute (i.e., ten feet per second), the sampler leading edges 40, 42 moves at approximately a 63 degree angle through the bulk material flow. Thus, for such an application, the downstream plate 36 forms an acute interior angle of about 63 degrees. During a pass of the sampler 28 across the belt 20 under the aforedescribed conditions, the bulk material backed up by the upstream side plate of the sampler 28 (as measured along the belt length) is approximately one foot.

Figure 5:
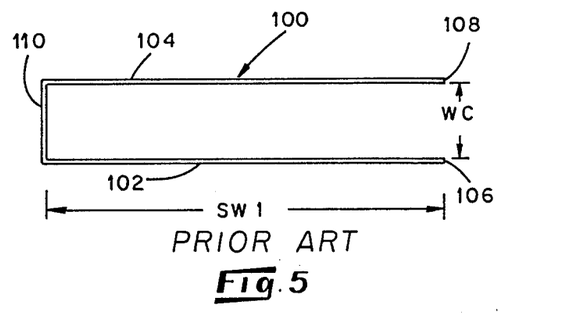
FIG. 5 is a view similar to that of FIG. 4 illustrating an alternative sampler of the prior art.

An advantage provided by the aforedescribed shape of the sampler 20 will become readily apparent when comparing it with the shape of a prior art sampler possessing a sample-accepting cavity of rectangular cross-section. For example, there is illustrated in FIG. 5 a prior art sampler 100 having parallel side plates 102, 104 with leading edges 106, 108 and a back plate 110 joining the side plates 102, 104. When moved leading-end first across the bulk material, an increment of the material is separated from the remainder of the bulk material by the side plates 102, 104 and swept from the conveyor belt by back plate 110. It follows that the width of a cross-stream increment of material segregated by the prior art sampler 100 is equal to the spaced-apart distance of the leading edges 106, 108, and the sample-accepting cavity of the sampler 100 is defined by the rectangular space, as viewed in cross-section in FIG. 5, bounded by the walls of the side plates 102, 104, back plate 110 and a plane containing leading edges 102, 104. The side width SW1 of the side plates 102, 104 may be about one-half the width of the belt 20 with which the sampler 100 is used, and the width of cut WC of the sampler 100 is normally not less than three times the largest opening through which 95 percent of the material will pass.

Figure 4:
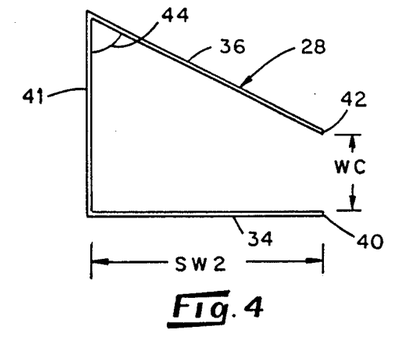
FIG. 4 is a cross-sectional view of the sampler of the FIG. 1 system taken along line 4—4 of FIG. 3.

For the sake of comparison, the spaced-apart distance of the leading edges 40, 42 of the FIG. 4 sampler 28 is equal to that of the leading edges 106, 108 of the FIG. 5 sampler 100 so that the width of cut WC through the bulk material by the samplers 28 and 100 are equal. It follows that in order for the cross-sectional area of the sample-accepting cavities of the samplers 28 and 100 to be equal for holding the same amount of bulk material), the side width SW2 of the FIG. 4 sample side plate 40 must be shorter than the side plate width SW1 of the FIG. 5 sampler 100. Because the volumetric holding capacities, in the case of the illustrated samplers 28 and 100, are directly proportional to the size of the corresponding cross sections, the upstream side plate 40 of sampler 28 can be made appreciably shorter in width than that of upstream side plate 102 of sampler 104 and the sampler 28 still provide a volumetric sample-accepting capacity which is at least as large as that of the sampler 100. Consequently, the surface area which the sampler 28 projects upstream of the bulk material flow is smaller than that of a prior art sampler of rectangular cross-section whose sample-holding capacity equals that of the sampler 28.

For purposes of further comparison, the following table is provided for illustrating the relative upstream side widths of the FIG. 4 and FIG. 5 samplers 28, 100 having a preselected cut width of six inches and cross sections, taken parallel to the axis of sampler rotation, having areas which are about equal.

TABLE 1

| | FIG. 4 SAMPLER With 63° Interior Angle 44 | | | FIG. 5 SAMPLER With Rectangular Cross Section | | |
|---|---|---|---|---|---|---|
| Belt Width (inches) | Cut Width CW (inches) | Side Width SW2 (inches) | Area (Sq. in.) | Cut Width CW (inches) | Side Width SW1 (inches) | Area (Sq. in.) |
| 24 | 6 | 7.6 | 60 | 6 | 9.8 | 58.8 |
| 30 | 6 | 9.0 | 74.3 | 6 | 12.25 | 73.5 |
| 36 | 6 | 10.7 | 92.8 | 6 | 15.0 | 90.0 |
| 42 | 6 | 12.0 | 108.0 | 6 | 17.8 | 106.8 |
| 48 | 6 | 13.4 | 125.1 | 6 | 20.5 | 123.0 |
| 54 | 6 | 14.6 | 140.9 | 6 | 23.1 | 138.6 |
| 60 | 6 | 15.8 | 157.2 | 6 | 25.8 | 154.8 |
| 72 | 6 | 18.0 | 189.0 | 6 | 31.1 | 186.6 |

Figure 6:
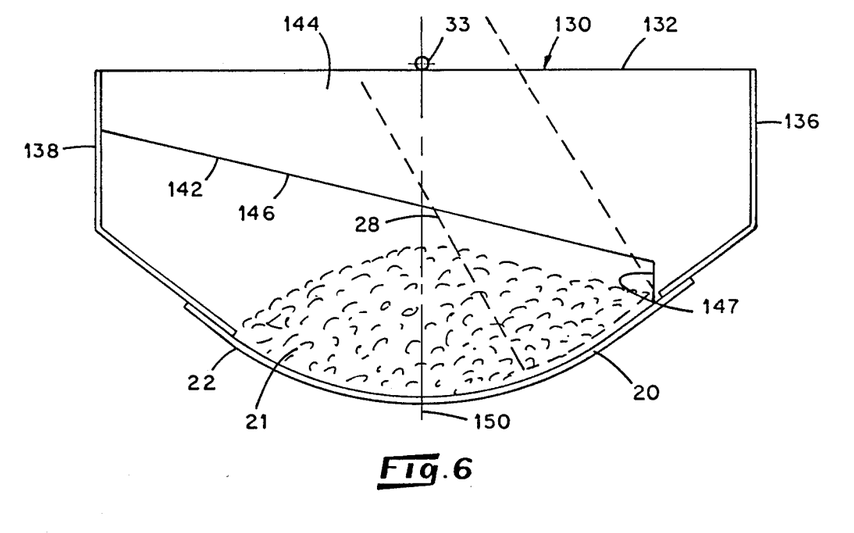
FIG. 6 is a frontal view of a surge dam from the FIG. 1 system illustrating its function during an increment-collecting cycle.

In another aspect of the present invention and with reference to FIGS. 1 and 6, the system 18 includes means for limiting the buildup of bulk material against the upstream side surface of the sampler 28 as the sampler 28 is moved through the bulk material. In the illustrated system 18, the limiting means includes a surge dam 130 in the form of a plate 132 positioned immediately adjacent to and upstream of the sampler 28, and oriented generally perpendicular to the path of bulk material flow. The dam 130 is supported at each end by a skirt arrangement 134 which is, in turn, appropriately mounted to the underlying belt supporting structure 27 in a manner maintaining the skirt arrangement in a fixed position relative to the structure 27. The skirt arrangement 134 includes side skirts 136, 138 extending along a section of belt length which includes the conveying reach 22. The side skirts 136, 138 are preferably constructed of stainless steel and do not appreciably retard the flow of material along the belt 20, even though the lower edges of the skirts 136, 138 may overlap the edges of the belt 20 and contact the edges of the load profile as illustrated in FIG. 6. One skirt 136, as best shown in FIG. 1, defines an opening or cutout 140 adjacent the frame structure 30 which accommodates passage of the sampler 28 therethrough during an increment-collecting cycle for subsequent ejection of the collected increment into the chute 29. During operation of the belt 20, the skirt arrangement 134 reduces any likelihood of spillage of the bulk material from the belt 20 in the vicinity of the frame 30 between increment-collecting cycles or during sampler stall.

As best shown in FIG. 6, the plate 132 of the surge dam 130 includes an upstream-projected face 144 having a lower edge 142 which is positioned above so as to span the upper surface of the bulk material moving along the belt 20. The lower edge 142 includes a major portion 146 which spans the upper surface of the bulk material 21 and extends angularly downwardly from side skirt 138. As bulk material builds up by a predetermined amount against the upstream side 40 of the sampler 28 and to the right, as viewed in FIG. 6, of the belt vertical midplane 150, the surge dam 130 intercepts the additional buildup and its lower edge 142 grades the bulk material buildup toward one side, or the left side as viewed in FIG. 6, of the belt 20.

The lower edge 142 also includes a vertically-oriented portion 147 extending downwardly from one end of the major portion 146 and positioned adjacent one side, or the right side as viewed in FIG. 6, of the belt 20. This vertical portion 147 prevents the material flow from extending outwardly beyond, or away from, the belt midplane 150 by a predetermined amount on the right side of the belt 20. Prevention of the rightward-extension of material flow can be important not only during a sampler cycle and/or a stall, but also when unusual surge loads occur with the sampler parked in its part position. Thus, excess loads which are significantly wider than normal are diverted by the plate edge portions 146, 147 toward the left side, as viewed in FIG. 6, of the belt 20.

As viewed in FIG. 6, the sampler 28 rotates about the shaft 33 in a counter-clockwise direction so that the sampler 28 enters the bulk material at the left side, or the sweep-entry side, of the belt 20 and exits the bulk material on the right side or the sweep-eject side of the belt 20. Experience has taught that in the unlikely event of a stall of the sampler 28 in the flow of bulk material as a result of the resistance to the passage of the sampler 28 therethrough brought about by a failure of the sampler driving mechanism, for example, the sampler 28 will almost always stall at a location illustrated in FIG. 6 offset from the belt midplane 150 and situated toward the eject-side of the belt 20. Such a location corresponds with the flow region of the greatest accumulated resistance and the flow region into which the sampler would fall in the event of a failure of the parking brake. Therefore, with the lower edge portion 146 of the plate 132 positioned closer to the load profile of the bulk material on the eject-side of the belt 20 than on the entry-side of the belt 20, the plate 132 is in condition to intercept bulk material once the material has flowed against the stalled sampler 28 by a predetermined amount and grades the surface of the bulk material to a condition corresponding with the slope of the edge portion 146.

Figure 7:
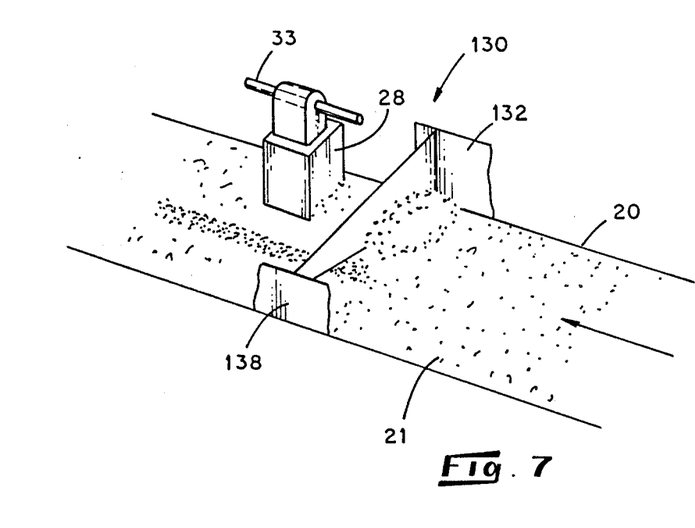
FIG. 7 is a fragmentary perspective view of the FIG. 1 system illustrating the buildup of material during a period in which the sampler is stalled in the path of material flow.
Figure 8:
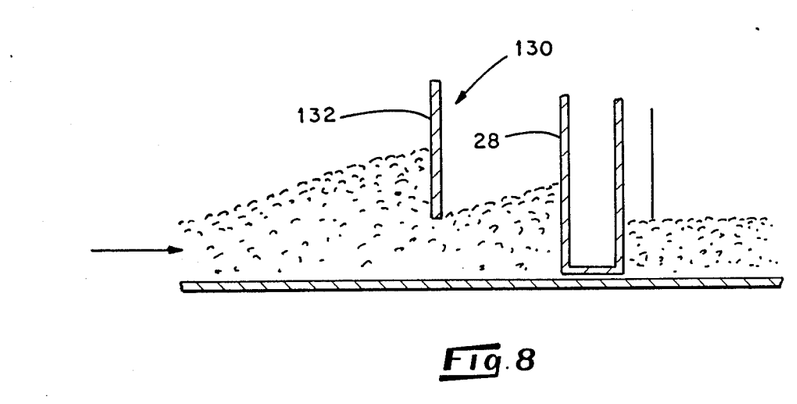
FIG. 8 is a longitudinal cross-sectional view of bulk material moving along the belt illustrating the buildup of material against the dam and samples during a pass of the sampler across the belt.

As best shown in FIG. 8, the height of the bulk material buildup against the sampler 28 is limited by the plate 132 positioned upstream of the sampler 28. In addition, because the left, or entry-side, of the plate edge portion 146 is higher than that of the right, or eject-side, of the plate edge portion 146, the dam 130 permits free flow of the excess material buildup on the eject-side of the plate 132 along the entry-side of the belt 20. Therefore and as illustrated in FIG. 7, the plate 132 effectively directs the excess material build up to a location along the belt width at which the material is permitted to continue its movement along the belt 20 and past the sampler 28. It follows from the foregoing that the plate 132 of the surge dam 130 intercepts any buildup of bulk material upstream of the sampler side 40 above a predetermined amount of material buildup so that downstream forces which would otherwise be exerted against the upstream side 40 of the stalled sampler 28 are diverted from the sampler 28 and instead transferred to the underlying belt support structure 27. This is of advantage also in a normal sampling procedure in limiting the height of material buildup against the sampler 28 as it passes through the material so that the sampler and its associated support structure are subjected to decreased thrust from the moving material.

As mentioned earlier and with reference again to FIG. 1, the opening 71 of the chute 69 disposed to one side, or the sweep or sample eject-side, of the belt 20 is in condition for receiving at any time bulk material removed from the belt 20 through the opening 140 defined in the side skirt 136. While it is, of course, necessary that the chute 69 receive the material increment removed from the belt 20 by the sampler 28, it is not desirable that the chute 69 accept material which may incidentally fall from the belt 20 through the skirt opening 140 between increment-collecting cycles due to the likelihood that a subsequently-taken sample will be biased by the fallen material. Therefore, in still another aspect of the invention, the sampler 28 is parked within the skirt opening 140 upon the completion of an increment-collecting cycle so as to inhibit any passage of material from the belt 20 into the chute 69 between increment-collecting cycles. It follows that the sampler 28 possesses such a size and shape in relation to that of the skirt opening 140 so that when positioned in its parked position, as illustrated in FIG. 2, the opening 140 is substantially blocked by the sampler 28. Blockage of the opening 140 is also enhanced by the engagement of the sealing member 54 with the surface of the belt 20 so as to prevent any passage of material through the opening 140 between the belt surface and the underside of the sampler 28. The parked position disclosed herein is also advantageous in that it enables the sampler 28 to be accelerated through an increased distance as compared to a vertical park position, to thereby achieve greater sampling speeds through the material on the belt.

For purposes of halting the sampler 28 in its FIG. 2 parked position, the control means 68 (FIG. 1) is appropriately preset so that the pneumatic cylinders 50, 51 cause the sampler 28 to be positioned in the parked position upon completion of a pass through material on the belt. To this end, the control means 68 closes an appropriate valve associated with one of the cylinders 50, 51 prior to the completion of an increment-collecting cycle so that the cylinder 50 or 51 acts as an air spring bumper which brings the sampler 28 to a sudden, but cushioned, stop at the precise location required to eject the sample increment in its optimum trajectory. During the stopping action of the sampler 28, the sampler 28 bounces back and forth between the two opposing cylinders 50, 51 before coming to rest at the desired park position. Such bouncing is advantageous in that any material which may otherwise stick inside the sampler 28 is shaken out. Once the sampler is parked, the control means 68 maintains the sampler 28, through the cylinders 50, 51 and braking means 54, in the parked position until the initiation of a subsequent increment-collecting cycle.

Although particular embodiments of the present invention have been described in the foregoing detailed description, it will be understood that the invention is capable of numerous rearrangements, modifications and substitutions without departing from the scope and spirit of the invention as set forth in the claims below.

What is claimed:

1. In a system for taking a sample of material carried on a moving conveyor belt wherein the sample is taken at a sampling location by passing a sampler across the belt through the moving material from an entry side of the belt to an exit side of the belt, the improvement which comprises means located upstream of the sampling location for limiting build-up of material against the sampler caused by the presence of the sampler within the flow of material so that only a predetermined build-up of material against the sampler is permitted to thereby limit the thrust force exerted against the sampler by the moving material in excess of that exerted when said predetermined build-up of material against the sampler is reached.

2. The improvement of claim 1, wherein said means for limiting build-up comprises dam structure supported adjacent the conveyor belt on dam structure support means, said dam structure including a plate spanning across the width of the belt upstream of the sampling location, said plate having a lower edge that is spaced from the material sufficiently to permit the material to clear the lower edge when no substantial build-up of material against the sampler is occurring and to intercept and thus limit the build-up of material against the sampler when substantial material build-up occurs.

3. The improvement of claim 2, wherein said lower edge of said plate includes a sloping portion that is sloped toward the belt as a path is traced from the entry side of the belt toward the exit side of the belt so that the surface of the material carried on the moving belt is graded toward the entry side by said sloping portion of said lower edge of said plate when build-up is intercepted along said sloping portion.

4. The improvement of claim 3, wherein said lower edge of said plate further includes a side portion that extends downwardly from said sloping portion to a point closely adjacent the upper surface of the belt on the exit side thereof and at a position that is closely adjacent to, but substantially outside of, the lateral edge of the material supported on the belt adjacent the exit side when no substantial build-up of material against the sampler is occurring, whereby expansion of the width of the material supported on the belt toward the exit side of the belt beyond said side portion of the lower edge of the plate occurring as a result of substantial material build-up against the sampler is restricted by said side portion.

5. The improvement of claim 1, further comprising skirt means disposed along and adjacent to the opposed side edges of the belt in the vicinity of the sampling location so as to restrict spillage of material from the belt in the vicinity of the sampling location.

6. In a system for taking a sample of material carried on a moving conveyor belt wherein the sample is taken at a sampling location by passing a sampler across the belt through the moving material from an entry side of the belt to an exit side of the belt, the improvement which comprises a plate supported upstream of the sampling location on plate support means and spanning across the width of the belt, said plate having a lower edge that is positioned to limit the height of the material on the belt in excess of a predetermined level as the material is carried on the belt through the sampling location.

7. The improvement of claim 6, wherein said lower edge of said plate includes a sloping portion that is sloped toward the belt as a path is traced from the entry side of the belt toward the exit side of the belt so that the surface of the material on the moving belt is graded toward the entry side of the belt by the sloping portion of the lower edge of the plate when the height of the material on the belt exceeds said predetermined level.

8. The improvement of claim 7, wherein said lower edge of said plate includes a side portion which extends downwardly from said sloping portion to a point closely adjacent the upper surface of the belt on the exit side thereof and at a position that is closely adjacent to, but substantially outside of, the lateral edge of the material supported on the belt adjacent the exit side when the height of the material on the belt has not exceeded said predetermined level, whereby expansion of the width of the material on the belt toward the exit side of the belt beyond said side portion of said lower edge of said plate occurring as a result of the height of the material on the belt exceeding said predetermined level is restricted by said side portion.

* * * * *